United States Patent [19]

Weetall

[11] 4,010,076
[45] Mar. 1, 1977

[54] REACTOR FOR STABILIZED MICROBES HAVING PHOTOMETABOLIC ACTIVITY
[75] Inventor: Howard H. Weetall, Big Flats, N.Y.
[73] Assignee: Corning Glass Works, Corning, N.Y.
[22] Filed: Apr. 1, 1976
[21] Appl. No.: 672,631
[52] U.S. Cl. .............................. 195/115; 195/116; 195/127; 195/139
[51] Int. Cl.² ........................................ C12B 1/00
[58] Field of Search .......... 195/104, 115, 116, 127, 195/139, 103.5 R; 47/1.4

[56] References Cited
UNITED STATES PATENTS 3,839,154   10/1974   Messing ............................. 195/127

Primary Examiner—A. Louis Monacell
Assistant Examiner—Robert J. Warden
Attorney, Agent, or Firm—James A. Giblin; Clinton S. Janes, Jr.; Clarence R. Patty, Jr.

[57] ABSTRACT

Useful products such as molecular hydrogen can be continuously produced by reacting a solution of a substrate in the presence of light with a photometabolically active microbe which has been stabilized on a support. In one embodiment, *Rhodospirillium rubrum* bacterial cells are mixed with agar gel and the mixture is spread over a plate which is placed in a transparent flow-through reactor. Then, an aqueous malate solution is passed through the reactor under essentially anaerobic conditions in the presence of light to yield molecular hydrogen. In another embodiment, Blue-Green algae are similarly stabilized for continuous biophotolysis of water by oxidizing the water and reducing NADP to NADPH. Other photosystems for producing useful products are disclosed.

13 Claims, 4 Drawing Figures

REACTOR FOR STABILIZED MICROBES HAVING PHOTOMETABOLIC ACTIVITY

BACKGROUND OF THE INVENTION

1. Field

This invention is concerned generally with the field of fermentation and specifically with the use of photometabolism (photosynthesis or biophotolysis) to produce useful products.

2. Prior Art

It is well known that certain microorganisms are capable of producing useful products in the presence of light and certain substrates. Typical of such organisms are the Blue-Green algae (e.g. *Anacystis nidulans*) which can be used to produce NADPH and certain bacteria which contain hydrogenase and/or nitrogenase enzymes and photosystems. Very generally, the production of products with such microbes involves the conversion (photometabolism) of certain substrates and/or the oxidation of a cofactor such as NADPH or compounds such as reduced ferrodoxins in the presence of a hydrogenase enzyme or a nitrogenase enzyme system. Since several reactants must be available to assure continuous photometabolic production, it can be appreciated that whole cells of photometabolically active microbes may be used to provide one or more contained enzyme systems.

It can also be appreciated, however, that if photometabolism is to be used as a large scale source of products or energy (e.g. $H_2$), there should be some manner of producing the products or energy on a continuous basis, thus requiring a highly stabilized photometabolically active microbe. It has now been found that such a stabilized microbe system is possible and the system can be used for the continuous production of useful products. Details of the method are described herein.

SUMMARY OF THE INVENTION

The method of producing useful products on a continuous basis comprises the steps of immobilizing whole cells of photometabolically active microbes on and/or within a support media such as agar gel to form a stabilized mixture, supportably placing the mixture within a light transmitting (essentially transparent or translucent) flow-through reactor, and, in the presence of light, passing through the reactor on a continuous basis a solution of a substrate which, with other substances, is capable of being photometabolized to yield a useful product. In one preferred embodiment, the microbes have hydrogenase and/or nitrogenase activity and are mixed with an agar gel to form a mixture which is thinly spread over the surface of a plate contained within the reactor, the plate being disposed in a manner to permit maximum light exposure to the microbes through the light transmitting walls of the reactor. A variety of gel-like materials may be used, if necessary, to stabilize the microbes; e.g. polymerized acrylamide, styrene, and acrylic acid. However, especially good results were observed with common agar. A preferred reactor comprises a hollow body having at least one light transmitting wall and an inner chamber within the body to which the light is transmitted. Inlet and outlet passageways communicate with the chamber and a support means for the immobilized, stabilized microbe system are within the chamber and disposed to receive the transmitted light.

SPECIFIC EMBODIMENTS

Figure 1:
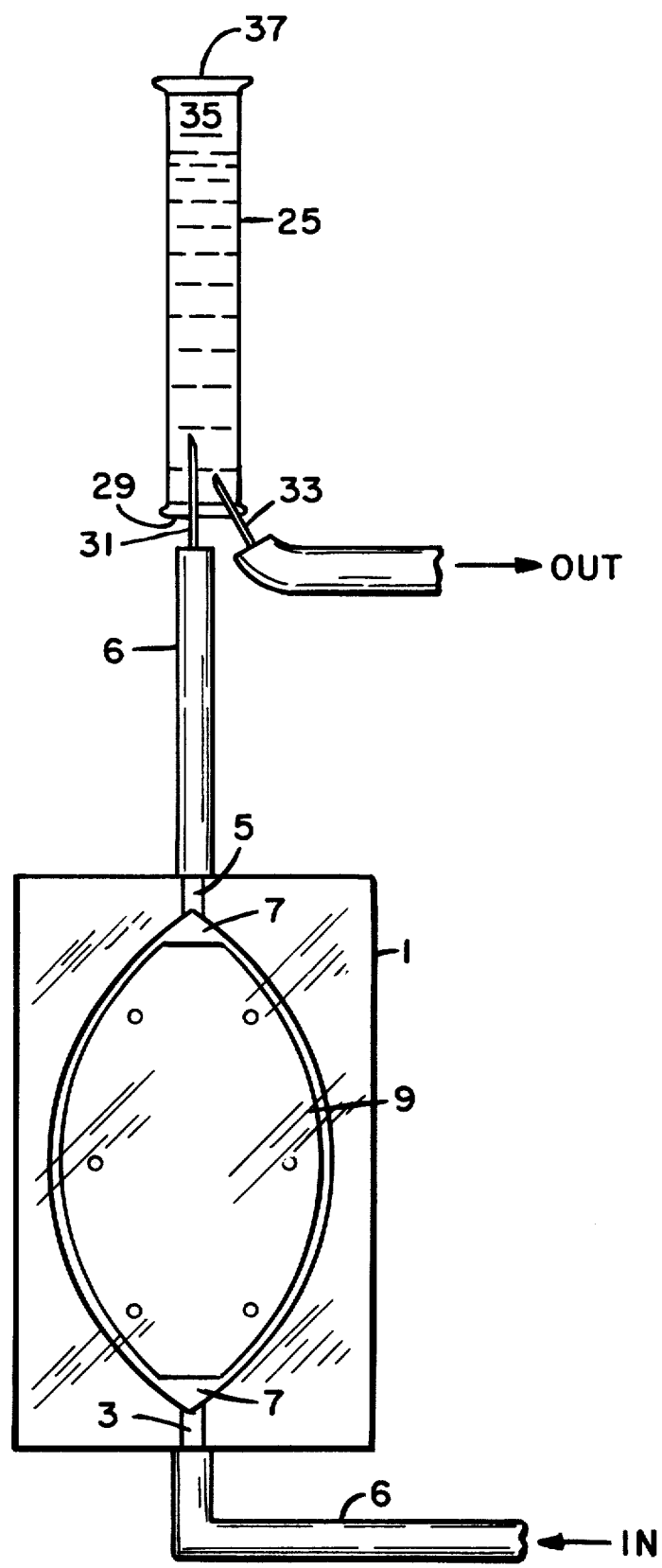
FIG. 1 is an illustration of the overall process showing a plate upon which a film of the stabilized microbes is held within an air-tight, transparent, flow-through reactor and a gas trap for gaseous product collection.

As used herein, the expression photometabolism or its equivalent refers to the use of light energy (visible electromagnetic radiation) in biochemical reactions of microbes to produce products photosynthetically and/or biophotolytically. Stabilized microbes, or the equivalent, refers to microbes which have been treated to retain a desired biological activity for a period of time greater than that of the microbe in its native state.

Examples of various photometabolically active organisms (microbes) having photosystems which can be harnessed for the continuous production of a useful product are given in the Table below.

TABLE I

| Organism | (Photosystems) System | Substrate | Product |
|---|---|---|---|
| Purple Bacteria | | | |
| Rhodospirillium rubium | Photoproduction | Malate | $H_2$ |
| Rhodospirillium rubium | " | ADP + P | ATP |
| Chromatium Sp. | " | Thiosulfate | $H_2$ |
| Chorombium thiosulfatophilum | " | $H_2S$ | $H_2$ |
| Choropseudomonas ethylicum | " | $H_2S$ | $H_2$ |
| Blue-Green Algae | Biophotolysis | | |
| Anacystis nidulans | (photosynthesis) | $H_2O$ | NADPH |
| Chorella Sp. | " | $H_2O$ | $H_2$ |
| Scenedesmus Sp. | " | $H_2O$ | $H_2$ |
| Chlamydomonas Sp. | " | $H_2O$ | $H_2$ |
| Ankistrodesmus Sp. | " | $H_2O$ | $H_2$ |
| Red Algae | " | $H_2O$ | $H_2$ |
| Chondrus Sp. | " | $H_2O$ | $H_2$ |
| Corallina Sp. | " | $H_2O$ | $H_2$ |
| Callilhamnion Sp. | " | $H_2O$ | $H_2$ |

In cases where the useful product produced is a reduced compound such as NADPH, a supply of that product can be continuously reacted with related microbe systems to yield alternate useful products. Representatives of such systems which do not require the use of light are shown in Table II.

TABLE II

| Organism | (Related Systems) System | Reduced Cmpds. | Products |
|---|---|---|---|
| Hydrogenomcnas Sp. | Hydrogenase | " | $H_2$ |
| Desulforibrio Sp. | " | " | $H_2$ |
| Clostridium Sp. | " | " | $H_2$ |
| Chromatium Sp. | " | " | $H_2$ |

From the above, it can be appreciated that the products produced via controlled and continuous photometabolism can be used directly or indirectly to supply other systems with substances which can be produced conveniently and abundantly.

Although a wide variety of photometabolically active microbes are known, the present invention can be readily illustrated with the Blue-Green algae *Anacystis nidulans* which oxidizes water and reduces NADP and the bacteria *Rhodospirillium rubrum* which oxidizes organic substrates such as malate to yield $H_2$. Other microbes having the hydrogenase and/or nitrogenase enzyme systems and, very importantly a photosystem, are described more fully in "Bioenergetics of Photosynthesis", Govindjee Ed., Academic Press, Inc., New York, N.Y. (1975). See especially p. 4 et seq.

It should be noted that certain photometabolically active microbes such as *R. rubrum* have "convertable" enzyme systems (e.g. hydrogenase/nitrogenase), the output of which will depend on the reaction environment. For example, in the presence of $NH_3$ or ammonium ions *R. rubrum* can be harnessed to produce $N_2$ on a continuous basis. On the other hand, if an appropriate organic substance is available for reaction, the same organism can be used to produce $H_2$. Hence, the desired useful end product will depend on the environment (reaction conditions) of the photometabolism. It is thought that, given this disclosure, the appropriate reaction environment can be readily determined and controlled. Hence, the reaction conditions sufficient to produce a given product are those conditions recognized by biochemists and others as being required to assure the production of a given product on a continuous basis.

*R. rubrum* is a nonsulfur, purple bacteria. It is known that maximal yields of $H_2$ are observed with resting cells in quantities closely approximating those predicted on the basis of complete conversion of certain organic compounds to $H_2$ and $CO_2$. See, for example, Burris, R. H., Proc. Roy. Soc. (Gr. Brit.) 172, 339 (1969). With malate, the reaction is as follows:

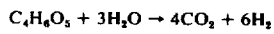

$$C_4H_6O_5 + 3H_2O \rightarrow 4CO_2 + 6H_2$$

Overall, the effect on the photometabolism of the organic substrate by $H_2$-producing *R. rubrum* is to divert carbon from the dissimilatory anaerobic citric acid cycle to assimilatory pathways.

EXAMPLE I

Use of Stabilized R. rubrum to Produce $H_2$

Preparation of the microbes

Cells of *R. rubrum* were grown in a medium described by Omerod, J. G. et al., Arch. Biochem. Biophys. 94, 449 (1961) and stored in the spent medium at 4° C until use. In the steps below, all batch experiments were carried out in a glove box filled with argon and, unless otherwise indicated, individual experiments were conducted with 5 ml flasks. After preparation, the flasks were stoppered and incubated 60–95 minutes on a mechanical shaker with constant illumination. Illumination was provided by two rows of 100 watt standard incandescent light bulbs. In the case of shaker flasks, the lights were placed under a large transparent LUCITE$^{TM}$ block into which the small flasks were placed. Aliquots of generated gas (usually 0.2 to 1.0 ml) were removed from the flask and assayed for $H_2$, $N_2$, and $O_2$ production on a Tracor 550 gas chromatograph using an 8 foot × ⅛ inch column having a 5 A molecular sieve.

Determination of $K_m$ of R. rubrum for Malate

A suspension of *R. rubrum* in 0.05M Tris, 0.001M $MgCl$ at pH 7.6 containing 600 mg wet weight/ml was prepared. One ml aliquots of the *R. rubrum* suspension were added to separate solutions of 1.0 ml of 0.1M to 0.001M malate solution. This was incubated in 5 ml flasks with constant illumination. The lights were positioned about 10 inches from the flasks.

Determination of Activity of R. rubrum

Several samples of *R. rubrum* were assayed in 0.01M malate at cell concentrations ranging from 20 mg wet weight/ml to 300 mg wet weight/ml as previously described. The $H_2$ production vs time was determined for each cell concentration.

Immobilization of R. rubrum

Four grams of *R. rubrum* wet weight was added to 15.0 ml of 5% solution of Noble Agar. This solution was spread evenly on both sides of a plastic plate (see FIG. 1 described below). The plate was put into an airtight, transparent system (described below) and 0.01M malate solution, continually purged with argon, was passed through the system in an upward flow at 8.0 ml/hr. The system was immersed in a water bath maintained at 18°–19° C. The gas produced was channeled to a double-ended glass tube (collector) that was kept air-tight by septums consisting of two serum vial tops. The malate solution was pulled through the collector with a syringe displacing any gas with substrate. Collection of the produced gas displaced the liquid. A sample was taken after the gas and the malate equilibrated and then a constant flow rate was re-established. Illumination was provided by a rack of seven 100 watt standard incandescent bulbs on each side of the reactor. The bulbs were positioned about 2 inches from the water bath containing the reactor and perpendicular to the plates contained therein and about 4 to 5 inches from the film of immobilized organisms.

Assay of Immobilized R. rubrum

A volume of 0.75 ml of gas was withdrawn from the collector. Of this amount, 0.5 ml was injected into the Tracor 550 Gas chromatograph. The quantity of $H_2$ produced ($\mu l$) was determined from a standard curve prepared with pure $H_2$. The percentage of $H_2$ in the 0.5 ml sample was then determined. The final quantity of $H_2$ was expressed in $\mu l$ $H_2$ produced/min. at a constant flow-rate of 8 ml/hr.

Description of the Reactor

Figure 2:
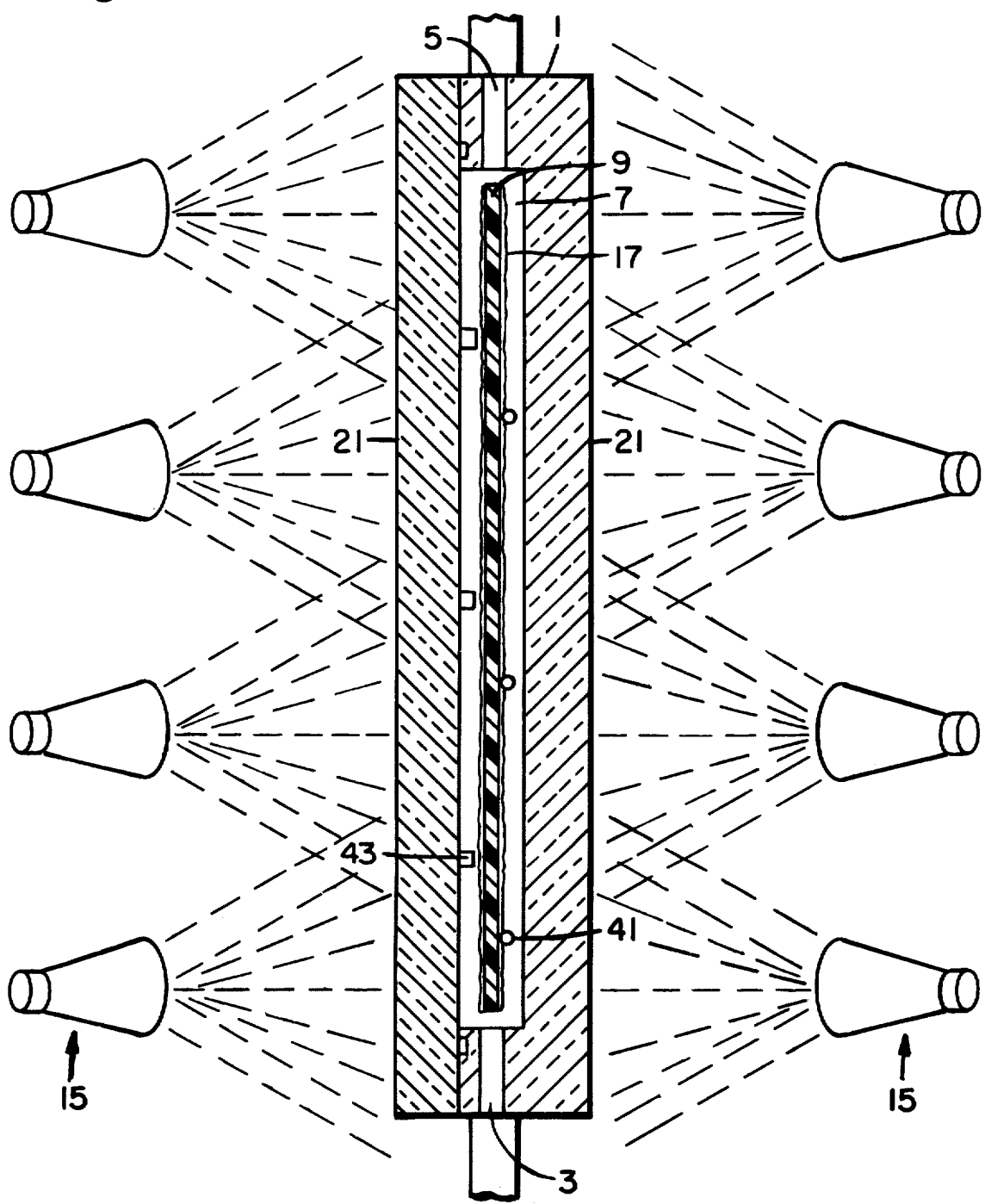
FIG. 2 is a side view of a reactor used to produce $H_2$ using stabilized *R. rubrum*.

The overall reactor system is described in FIGS. 1 and 2. In FIG. 1, a hollow, transparent reactor 1 is shown with inlet 3 and outlet 5 passageways to which conventional air tight tubing 6 can be sealably attached. Within reactor 1 is a reactor chamber 7 through which aqueous solutions of substrates must pass in proceeding from inlet 3 to outlet 5. Within chamber 7 is a plastic plate (slab) 9 which, in one actually constructed model, was somewhat oval in shape, about 4 inches by 8 inches and about ¾ inch thick. On both opposing sides of plate 9 (See FIG. 2) is thinly spread the agar — R. rubrum mixture 17 such that a film about 1 to 2 mm thick covers both of the larger surfaces of the slab 9. Disposed about 6 inches from the reactor 1 are two banks of lights 15 positioned to provide maximum illumination to the slab surfaces 9 upon which the agar — R. rubrum mixture 17 is thinly spread. Both walls 21 of reactor 1 facing the banks of lights 15 must be essentially transparent or translucent to permit maximum transmittance of photometabolically useful light therethrough to the reactor chamber 7. In one specific embodiment, illustrated by FIG. 1, the reactor housing was made from transparent LU-CITE plastic although it can be appreciated that other transparent or translucent light transmitting materials (e.g. glass) may be used. Also, it should be understood that the amount of surface area of the film 17 exposed to the light may be readily modified or increased (e.g. by changing the surface configuration of the plate).

In one operation, using the R. rubrum, a suitable photometabolizable substrate solution is introduced through inlet 3 on a continuous basis. As the microbes on and within the film 17 respond to the light from the light banks 15 and reactants, $H_2$ gas (a useful gaseous product) is formed. The gas passes through outlet 5 through connecting tubing 6 where it passes into gas collector 25. Gas collector 25 consists of a cylindrical tube opened at both ends. In the lower end, a septum 29 retains the substrate solution while permitting entrance 31 and exit 33 of the substrate solution on a continuous basis. Gases 35 collect in the upper portion of the gas collector and are trapped by a second septum 37 through which gas samples may be conveniently removed by a variety of methods (e.g. syringe needle which penetrates through the septum). It should be appreciated that FIG. 1 is subject to obvious variations and the Figure merely illustrates the set up actually used with the stabilized R. rubrum. FIG. 2 illustrates in greater detail and in cross sectional side view the reactor 1 of FIG. 1 and all numbers correspond to similar parts in both Figures. Glass beads 41 (about 2 to 3 mm in diameter) and projections 43 act as spacers keeping the slab 9 spaced away from the insides of reactor walls 21 so that the incoming substrate can readily flow over and be acted upon by film 17 in the presence of light from banks 15.

Kinetics of Hydrogen Production Production from Malate

Figure 3:
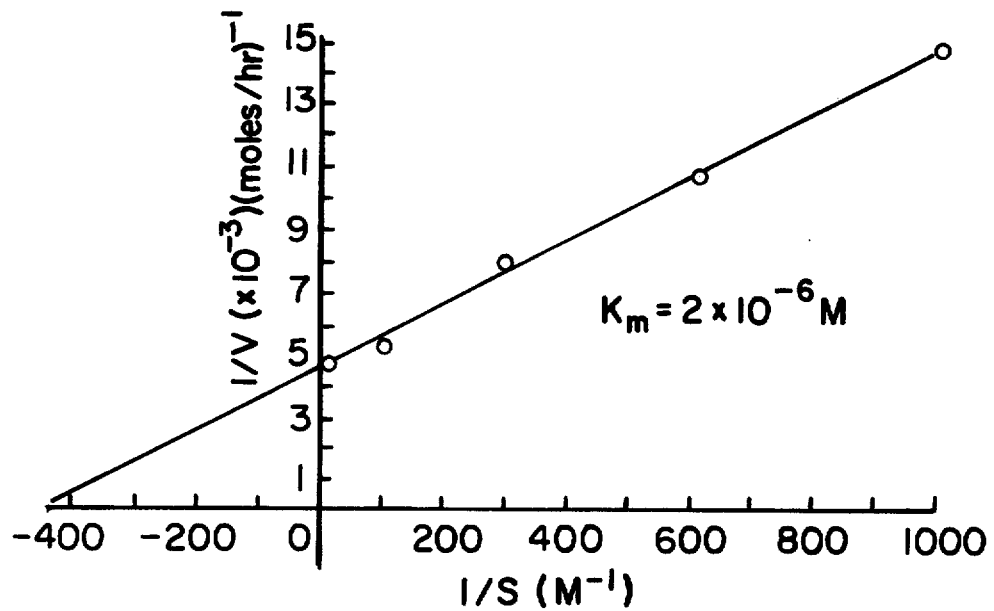
FIG. 3 is a graph summarizing Km studies for the stabilized *R. rubrum*.

It was found that the R. rubrum would produce reasonable quantities of $H_2$ at concentrations above 120 mg wet weight/ml. Additional experiments indicated the most efficient combination of variables and a standard method for assaying was as follows: 1 ml R. rubrum (300–500 mg wet weight/ml), 1.0 ml 0.01M malate solution, and constant illumination for 90 minutes which yielded 3.5–5.7 $\mu l$ $H_2$ in a 0.5 ml sample taken from a 5 ml flask. These conditions were determined from the $K_m$ studies (see FIG. 3).

Immobilized R. rubrum

Figure 4:
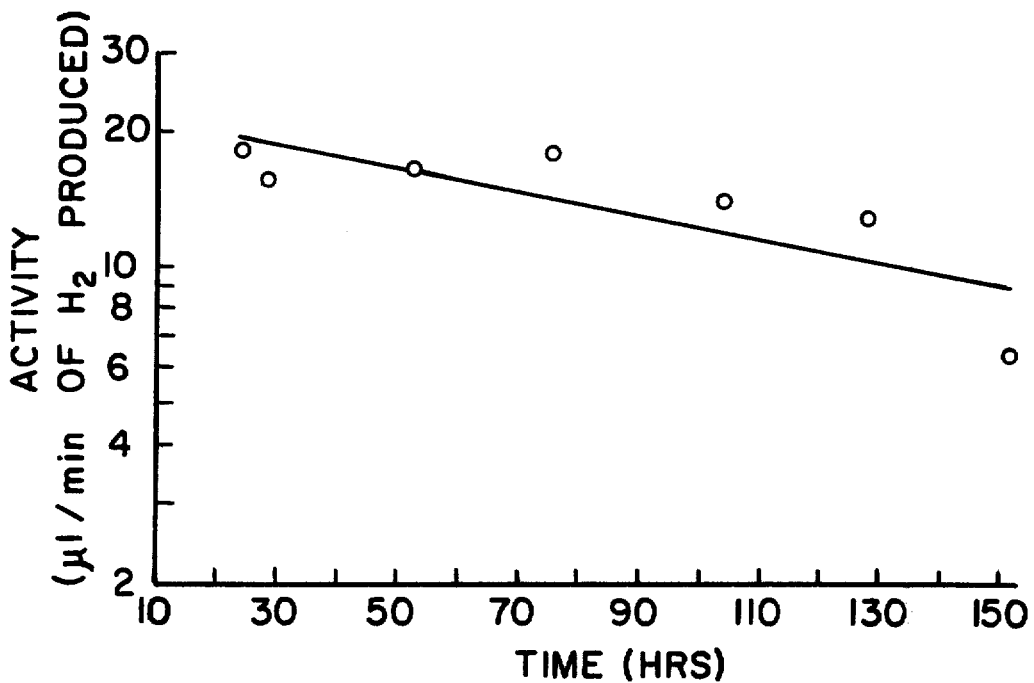
FIG. 4 is a graph summarizing the results obtained in making useful products with the reactor illustrated by FIGS. 1 and 2.

The results from a typical reactor are given in FIG. 4. The reactor operated for 150 hours producing a maximum of 22.01 $\mu l$ $H_2$/min. The total $H_2$ produced during the first half life ($t \frac{1}{2}$) of operation was $1.09 \times 10^5$ $\mu l$. One reactor reached a high of 45 $\mu l$ $H_2$/min. This reactor contained a higher quantity of bacteria and gave an initial increase in activity before exponential decay was observed. In FIG. 4, the data are interpreted as follows:
Slope = —0.006
Std. Error = 0.232
Correl = —0.8136
Max. $H_2$ production rate (at time = 0) = 22 $\mu l$/min.
95% UCL ($T_{1/2}$) = 641.8 hrs.
$T_{1/2}$ = 114.5 hrs.
95% LCL ($T_{1/2}$) = 62.84 hrs.

In the case of the R. rubrum, it was found that active preparations of the stabilized microbe were obtained only if handled under anaerobic conditions. Some difficulty was encountered in preparing identical preparations for the reactor particularly in regard to the thickness of the agar layer. A preferred film thickness is about 0.1 to 2.0 mm but variation in thickness resulted in variations in reaction rates due to diffusion and in apparent half-lives. In a few case half-lives as low as 35 hours were observed. However in these cases it is believed that $O_2$ contamination played a major role in the observed results.

It is clear from the above example, however, that whole cells of R. rubrum can be immobilized in an active form and that they will produce $H_2$ on a continuous basis.

EXAMPLE II (Stabilized Algae)

Blue-Green algae (Anacystis nidulans) were stabilized in a manner similar to that used for the R. rubrum, and then half life studies on the biophotolysis of the algae were done by monitoring the reduction of NADP (TPN) to NADPH (TPNH) using the same reactor described above. In this case, the NADPH is deemed a useful product since it can be used in other enzymatic reactions as an energy source and/or to provide a source of NADP which can be used in other systems, (e.g. be reduced in another cycle). The algae were stabilized by first preparing a 5% agar solution in 0.5M tris buffer. When the agar cooled to near solidification temperature, about 20 ml of 5% agar was mixed with about 0.2 grams of the algae in a freeze dried condition. It was found that by adding some gluco-oxidase (~15,000 units per gram) at a concentration of 0.1% in the buffer which contains the substrate, the half life of the stabilized algae can be increased substantially. Also, a small amount of catalase (in a 3 to 1 w/w ratio of glucose oxidase to catalase) and 0.01% dextrose was added to the buffer.

The system used to determine half lives of the stabilized algae system consisted of the reactor containing about 20 ml of the agar-algae mixture through which substrate flowed at a rate of 12–15 ml/hr. at 18° C.

In the above system, the glucose-oxidase and catalase act as an $O_2$ scavenger system. When dextrose was added at concentrations of 0.1% and 1.0%, the variations in concentration did not seem to have an effect on half life. Arbitrary activity units were used to determine half life of the stabilized system and the results of four studies are summarized in Table III.

The half life results of the Table represent four runs (A through D) made with the gel mixture under continuous operating conditions. The substrate, consisting of a solution of 419 mg NADP, 0.5 M TRIS, dextrose (glucose) at the desired concentration, 1500 mg of the glucose oxidasecatalase preparation in 500 ml total aqueous volume, was passed through the column once and the NADPH produced was determined fluorimetrically at 460 nm with the excitation wavelength at 340 nm. Samples A, B, and C had the glucose oxidase-calalase present as an $O_2$ scavenger and half life values were higher for those samples. The glucose (w/v) concentrations correspond to 1 mg/ml (0.1%) and 10 mg/ml (1.0%), respectively.

The numbers in the Table include half lives in hours, 95% upper (UCL) and lower (LCL) confidence limits in hours, and the correlation of the data via regression technique.

TABLE III

| | | (Half-Life Studies In Hours) | | | |
|---|---|---|---|---|---|
| Sample | Glucose conc. (w/v) | $T_{1/2}$ | UCL | Hours LCL | Correl. |
| A | 0.1% | 12.6 | 13.7 | 11.7 | 0.987 |
| B | 0.1% | 8.0 | 8.6 | 7.5 | 0.992 |
| C | 1.0% | 10.5 | 10.8 | 10.3 | 0.998 |
| D | 0 | 2.6 | 3.0 | 2.3 | 0.968 |

It can be appreciated that where non-gaseous useful products such as NADPH are produced, the gas trap of FIG. 1 is not needed and the product can be isolated and collected by conventional means after it emerges from the reactor.

Inasmuch as the above examples are illustrative only, it is intended that the above-described invention should be limited only by the following claims.

I claim:

1. A method for the continuous photometabolic production of a useful product which comprises the steps of immobilizing whole cells of a photometabolically active organism on a medium to form a stabilized composite, supportably placing the composite within a reactor having at least one light transmitting wall, and, in the presence of light being transmitted through the wall, continuously passing into the reactor a substance capable of being photometabolized by the cells under conditions sufficient to assure the production of the useful product.

2. The method of claim 1 wherein the whole cells are bacterial cells.

3. The method of claim 2 wherein the bacterial cells are cells of *Rhodospirillium rubrum* and the medium on which the cells are immobilized in a gel-like material.

4. The method of claim 3 wherein the gel-like material is agar.

5. The method of claim 4 wherein the substance being photometabolized is an aqueous malate solution and the product produced is molecular hydrogen.

6. The method of claim 1 wherein the whole cells are algae cells.

7. The method of claim 6 wherein the algae cells are cells of *Anacystis nidulans* and the cells are immobilized on a gel-like material.

8. The method of claim 7 wherein the gel-like material comprises agar.

9. A reactor for the continuous photometabolic production of a useful substance comprising, in combination, a hollow body having at least one light transmitting wall and an inner chamber, inlet and outlet passageways in communication with the inner chamber and the environment external to the body, and, disposed within said chamber and, in communication with said inlet and outlet passageways, a support means supporting an immobilized, photometabolically active microbe system, said system disposed in a position to receive light transmitted through the light transmitting wall.

10. The reactor of claim 9 wherein the immobilized microbe system comprises a mixture of a gel-like material and a microbe selected from bacterial *Rhodospirillium rubrum* and algal *Anacystis nidulans*.

11. The reactor of claim 10 wherein the gel-like material is agar and the microbe-agar mixture is a film thinly spread over support means within the reactor chamber.

12. The reactor of claim 11 wherein the film ranges from about 0.1 to 2.0 mm in thickness.

13. The reactor of claim 9 wherein gas collection means are in closed communication with the chamber outlet passageway.

* * * * *